United States Patent [19]

Landwehrkamp et al.

[11] Patent Number: 5,420,439

[45] Date of Patent: May 30, 1995

[54] PROCESS TO DETECT AND COUNT YARN DEFECTS HAVING A COLOR BACKGROUND AND A CAMERA

[75] Inventors: Hans Landwehrkamp, Lenting; Inge Stöckert, Münchsmünster, both of Germany; A. A. Ball, Charleston, S.C.; Thorsten Büchner, Ingolstadt, Germany; Wolfgang Thierron, Kösching, Germany; Sohrab Tabibi, Reutlingen, Germany; Heinz Müller, Metzingen-Neuhausen

[73] Assignee: Rieter Ingolstadt Spinnereimaschinenbau Ag, Ingolstadt, Germany

[21] Appl. No.: 211,149

[22] PCT Filed: Sep. 1, 1992

[86] PCT No.: PCT/EP92/02005

§ 371 Date: Mar. 22, 1994

§ 102(e) Date: Mar. 22, 1994

[87] PCT Pub. No.: WO93/06466

PCT Pub. Date: Apr. 1, 1993

[30] Foreign Application Priority Data

Sep. 23, 1991 [DE] Germany .................. 41 31 664.9

[51] Int. Cl.$^6$ .............................................. G01N 21/88

[52] U.S. Cl. .................................. 250/572; 356/238; 242/36

[58] Field of Search ............... 250/572, 571, 561, 562; 356/238; 57/265, 264; 242/29, 36

[56] References Cited

U.S. PATENT DOCUMENTS 2,592,039  4/1952  Laetsch et al. .
5,220,178  6/1993  Dreiling et al. ............ 250/572
5,315,367  5/1994  Salvador et al. ............ 356/238

FOREIGN PATENT DOCUMENTS

3928279A1  2/1991  Germany .

Primary Examiner—David C. Nelms
Assistant Examiner—Que T. Le
Attorney, Agent, or Firm—Dority & Manning

[57] ABSTRACT

A process and device to detect and count yarn defects in a yarn segment including a camera (5), a computer (8) and an image processing program. The yarn (30) is illuminated with an intensity dependent upon the thickness of the yarn (30) and is photographed by the camera (5). The photographed image is digitalized in the computer with the image processing program and low-contrast points are filtered out. The remaining points are gathered together into coherent areas the sizes of which are classified into predetermined size classes and are stored.

25 Claims, 5 Drawing Sheets

PROCESS TO DETECT AND COUNT YARN DEFECTS HAVING A COLOR BACKGROUND AND A CAMERA

BACKGROUND OF THE INVENTION

Gravimetric processes and manual counting processes were known in the past for the detection of yarn defects caused by impurities. Gravimetric processes are based on the collection and weighing of eliminated trash particles during the spinning process, e.g. on a rotor spinning machine. This does however not indicate how much trash still remains in the finished yarn nor the type of impurities remaining.

Also known are manual counting processes to ascertain how many trash particles are in the yarn. For this purpose the spun yarn is knit on a circular knitting machine and a certain surface is cut out of the knit material. A grid is placed on the cut-out surface and the number of trash particles in the individual areas is counted. The disadvantage of this system is the great amount of time necessary to prepare the knit material and then to count the particles. It is also a disadvantage that the success of the process depends very much on the accuracy of person doing the counting. Comparisons have shown that examinations of the same knit material by different persons show very different counting results.

OBJECTS OF THE INVENTION

It is a principal object of this invention to create a rapid, objective and reproducible method to count the trash particles and other yarn defects or impurities in the yarn. Additional objects and advantages of the invention will be set forth in part in the following description, or may be obvious from the description, or may be learned through practice of the invention.

Advantageous embodiments of the invention are shown in the accompanying drawings.

DETAILED DESCRIPTION OF THE PREFERRED EMBODIMENTS

Figure 1:
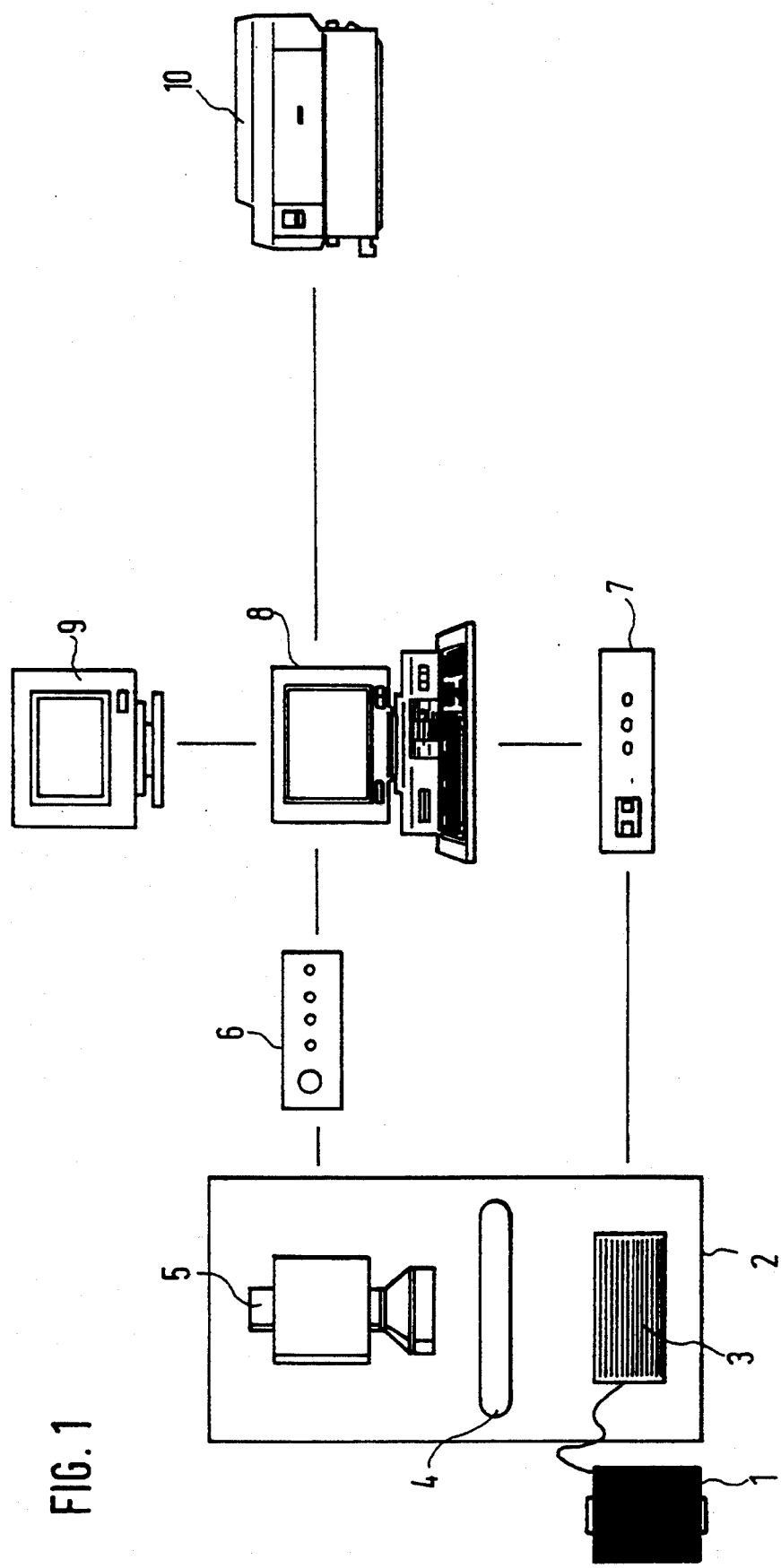
FIG. 1 shows a layout of the devices used for optical yarn analysis.

Reference will now be made in detail to the presently preferred embodiments of the invention, one or more examples of which are illustrated in the accompanying drawings. Each example is provided by way of explanation of the invention, and not as a limitation of the invention. For instance, features illustrated or described as part of one embodiment can be used on another embodiment to yield a still further embodiment. Additionally, the numbering of components in the drawings is consistent throughout the application, with the same components having the same number in each of the drawings.

FIG. 1 shows a schematic sketch of a device for optical yarn analysis. The yarn to be examined is wound up on a bobbin 1. For the examination the yarn is introduced through an opening into a housing 2. In order to avoid influences due to external light, the housing 2 is made light-tight in an advantageous embodiment. This ensures that a wind-up unit 3 can be illuminated evenly in incident light by a light source 4. The light-tight housing 2 prevents any additional light sources from influencing the wind-up unit 3 from the outside and thus possibly to cast shadows which the system would erroneously recognize to be yarn defects. The wind-up unit 3 is either a conventional yarn plate or an automatically driven device according to the invention such as described in further detail in FIGS. 2, 3, and 4.

The light source 4 in this case is advantageously a fluorescent bulb. Two concentric ring-shaped fluorescent bulbs have shown to be especially well suited here. Such a light source 4 ensures even, shadowless illumination of a testing surface on the wind-up unit 3. If the light source 4 is an infrared light, trash and other yarn irregularities which are inside the yarn, and not only those located on the outside and on the visible side of the yarn, can be detected. A camera 5 is installed above the light source 4. This is preferably a CCD camera. CCD cameras have the advantage that they are able to take a picture very precisely, are insensitive to electromagnetic interference radiations, and produce no drop-off of luminosity towards the edge of the picture. Very brief exposure times are sufficient with a CCD camera. However longer exposure times still do not cause the photographed scene to be burned in on the target of camera 5. Cameras of this type can therefore be used in continuous operation over very long periods of time while optimal image quality is maintained.

The camera 5 is connected via a camera controller 6 to a computer 8. The power supply for the CCD camera 5 as well as selection of the type of operation are located in the camera controller 6.

The wind-up unit 3 is connected to the computer 8 via a wind-up control 7. The wind-up control 7 determines when and how the winding of the wind-up unit 3 is to be modified. The individual control processes are shown in greater detail in FIG. 4.

To display the yarn defects detected in the yarn analysis device, a graphics screen 9 and a printer 10 are connected to the computer 8. The image photographed by the camera 5 is reproduced on the graphics screen 9. The different detected yarn defects are marked on the graphics screen 9 so that the operator is able to ascertain whether particles, and if any, which particles were detected by the system, in particular in order to adjust the device. If the operator sees that impurities in yarn 30 which are visible to the naked eye are not recognized by the system, finer tuning is required in order to modify the system's trash particle recognition. The results of the analysis can be printed out on the printer 10.

Instead of the yarn 30 from bobbin 1 and from the wind-up unit 3, it is also possible to present a woven or knit material to the yarn analysis system to be analyzed. A presentation for analysis of this type also falls within the framework of the invention.

Figure 2:
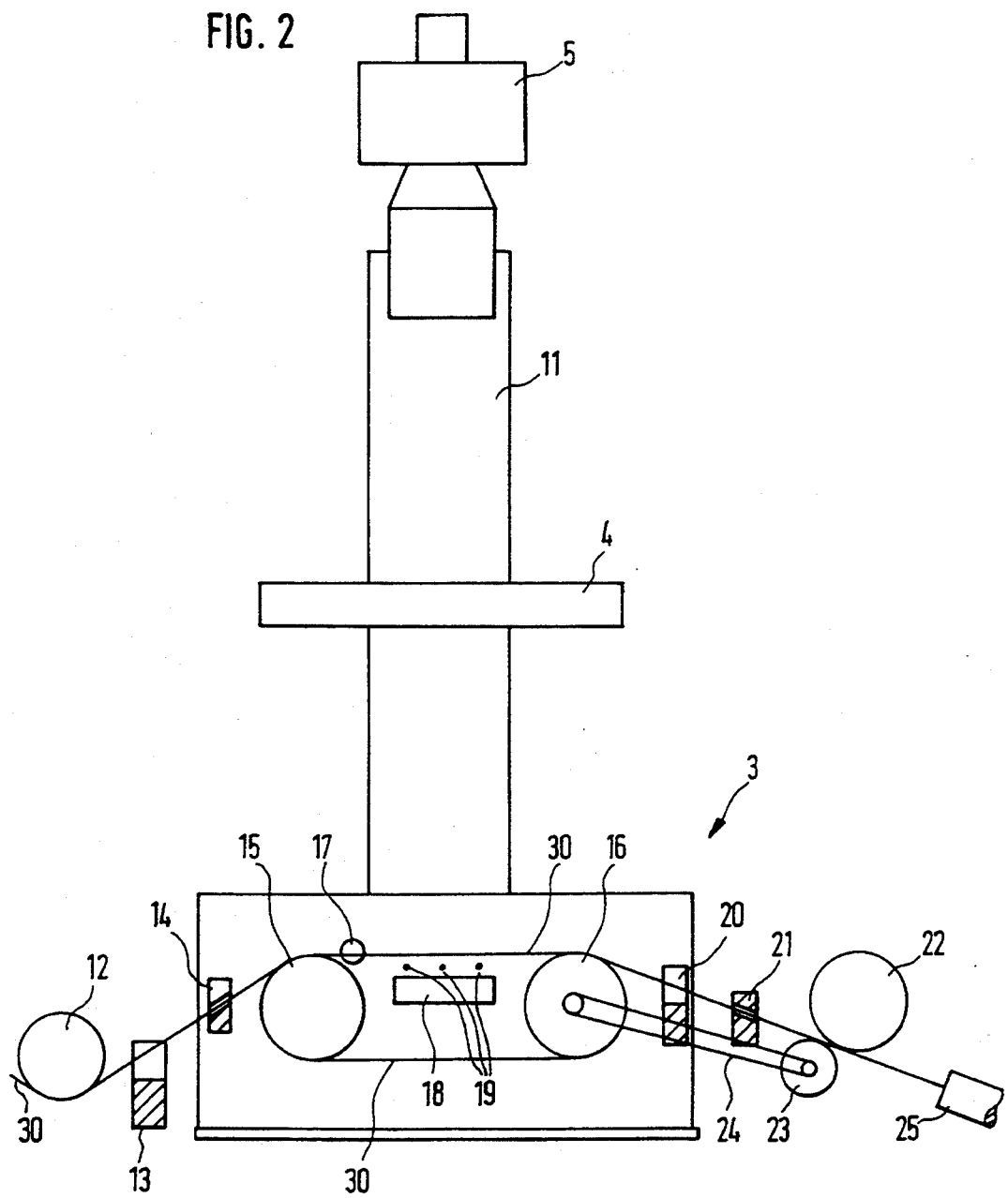
FIG. 2 shows a measuring instrument for yarn analysis.

FIG. 2 shows the basic layout of the measuring instrument contained in housing 2. The camera 5 and the light source 4 are fastened to a stand 11. In an advantageous embodiment, the lens of the camera 5 is pointing through the center of two concentric fluorescent lights of different diameter. The intensity of the light source can be changed by means of a dimmer. Intensities between 700 lux and 1600 lux have proven to be advantageous, with thicker yarns requiring the greater intensities.

The light source can also consist of a homogenous illumination placed at the side of the measuring instrument. The illumination of the measured surface may be ensured by a semi-permeable mirror which directs the light rays upon the measured surface on the one hand, and makes it possible on the other hand to take the picture by means of the camera.

The camera 5 is aimed at an area between two rollers 15, 16 between which a background surface used as a contrast surface 18 is placed. The yarn 30 is located between the camera 5 and the contrast surface 18, at a short distance from the contrast surface 8.

The yarn 30 is conveyed to the measuring instrument via a yarn brake 12. This ensures that sufficient tension is always present in the yarn 30. Following the yarn brake 12, a yarn monitor 13 is provided in the path of yarn 30. The yarn monitor 13 verifies the presence of the yarn 30. As soon as the yarn monitor 13 ascertains that no more yarn is being conveyed to the measuring instrument, it automatically shuts off the machine. In order to ensure orderly transportation to the contrast surface 18, a guiding eyelet 14 is provided directly before the roller 15. The yarn 30 runs through this guiding eyelet 14 and over roller 15 into a dividing mechanism 17 and then over roller 16. The yarn 30 is deflected at the roller 16 and is taken back to the roller 15. As it passes again through the dividing mechanism 17, a defined distance from the preceding yarn winding is maintained. This winding around the rollers 15 and 16 with the passage through the dividing mechanism 17 is repeated until a sufficiently large yarn surface is provided to be acquired by the camera 5. It has proven to be advantageous for the measuring field to be slightly larger than the filed photographed by the camera 5, as in that case uneven illumination at the edge of the measuring field or unwanted light intrusions are eliminated.

To photograph the yarn wound around rollers 15 and 16, a measuring field with dimensions of approximately 55×40 mm has been shown to be advantageous. With a distance between the individual yarn windings of approximately 0.7 mm, approximately 3 m of the yarn 30 are measured per photograph.

After the last winding, the yarn 30 is led off roller 16 through a yarn monitor 20. This yarn monitor 20 verifies the presence of the yarn as does the yarn monitor 13. If the yarn monitor 20 does not register the presence of yarn, this is a signal for the measuring instrument that the yarn withdrawal is not taking place in a correct manner. The measuring instrument is then switched off. The yarn 30 runs through a guiding eyelet 21 following the yarn monitor 20. The guiding eyelet 21 ensures that the yarn 30 is fed correctly to a draw-off device with a pressure roller 22 and a draw-off roller 23. The yarn 30 which leaves the measuring instrument via the draw-off device is conveyed to a yarn sucking pipe 25 in the embodiment shown. The yarn sucking pipe 25 guides the yarn 30 into a waste container which is not shown here. It is however also possible to feed the yarn 30 to a reeling device instead of the waste container and to wind it up on a bobbin.

The roller 15 is advantageously made in the form of a friction roller. This means that it is not driven autonomously but is rotated by the yarn windings which surround it and move as a new yarn grouping is brought into position to be measured. The roller 16 however is an autonomously driven roller. Here it assists the forward motion of the yarns through the draw-off device.

The dividing mechanism 17 is placed between the rollers 15 and 16. In an advantageous embodiment, the dividing mechanism 17 consists of a plurality of disks in a row, each being separated from the other by a spacer of lesser diameter.

Blowing nozzles 19 are placed between the parallel yarn windings and the contrast surface 18. The contrast surface 18 is cleaned before each measuring process by means of the blowing nozzles 19 which are directed upon the top of the contrast surface 18. In this manner an erroneous indication of the measuring instrument due to dirt on the contrast surface 18 is avoided.

The driven roller 16 is connected via a toothed belt 24 to the draw-off roller 23 of the draw-off device. Thus, synchronized movement is ensured in a simple manner between roller 16 and draw-off roller 23. This is necessary to avoid yarn breakage in the measuring instrument. A controlled transmission between the driven roller 16 and the draw-off roller 23 can cause the draw-off roller 23 to convey the yarn 30 at the same speed as in the winding device. The yarn 30 is thereby constantly held under tension in the wind-up unit 3, so that no distortion will occur as the yarn grouping is received in the measuring field. The pre-stressing of a spring causes the pressure roller 22 to be pressed against the draw-off roller 23 and ensures slip-free withdrawal of yarn 30.

Figure 3:
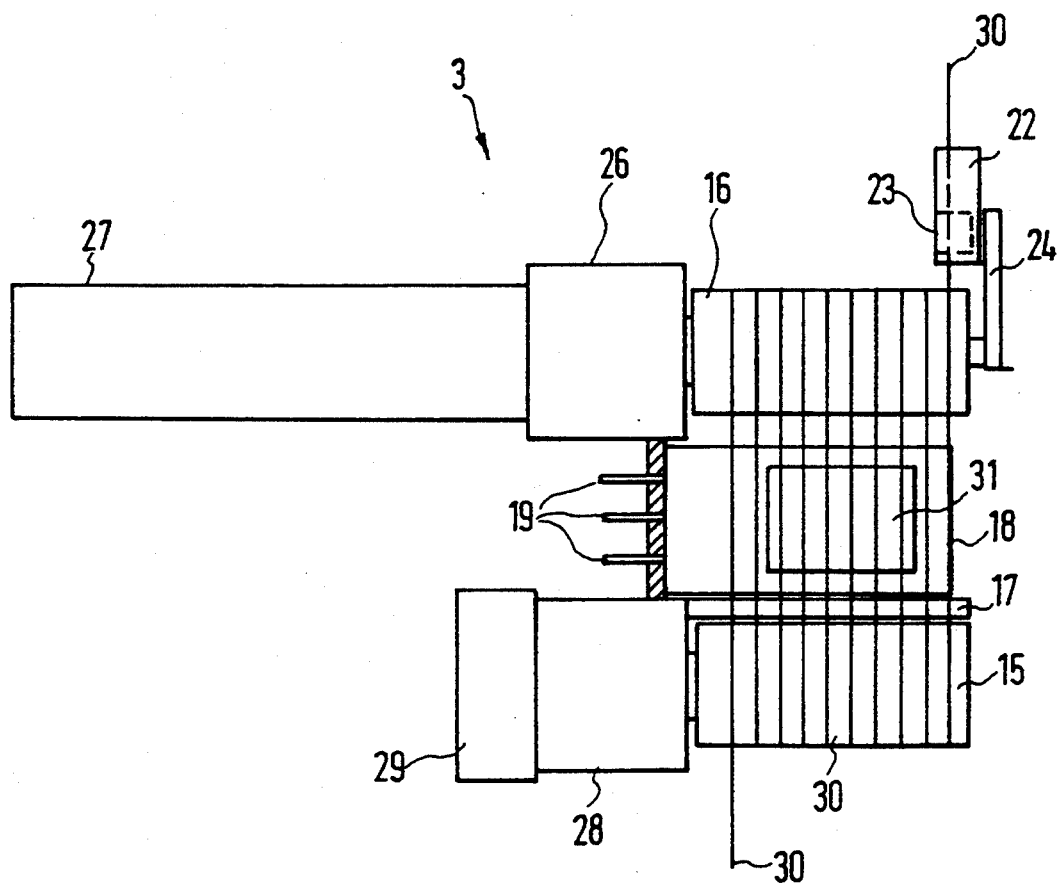
FIG. 3 shows a winding device.

FIG. 3 shows a top view of a wind-up unit 3. A contrast surface 18 is located between the rollers 15 and 16. If the yarn 30 is examined for trash contents, it has been shown to be advantageous to use a white contrast surface 18, as the white yarn recedes optically in that case by comparison to the dark trash. If however light yarn defects which are not caused by trash are to be found in the yarn, a black background is advantageous to bring out these defects.

The contrast surface 18 can be subjected to lateral blowing by nozzles 19 for cleaning purposes. The yarn windings wound around the rollers 15 and 16 can be recognized above the contrast surface 18. For this purpose the yarn 30 is fed on the side of the non-driven roller 15 to the measuring instrument and is withdrawn form the measuring instrument by the draw-off device on the side of the driven roller 16. The division of the individual windings is maintained constant by the dividing mechanism 17. The roller 15 is over-mounted in a bearing 28. An initiator 29 is provided on the roller 15 to ascertain whether the reeling device is stopped and whether the yarn 30 is thereby correctly positioned to be photographed by the camera 5.

The roller 16 is over-mounted in a bearing 26. The roller 16 is driven by a motor 27. A permanently excited d.c. servomotor with a maximum rotational speed of 6000 1/min has shown to be advantageous. With such a motor, precise starting of defined segments of the yarn windings is achieved.

A field 31 is shown on the contrast surface 18. The field 31 defines the surface in which the camera 5 takes a picture. By driving the yarn 30 by means of motor 27, the photographed yarn grouping is moved out of field 31 and a new yarn grouping or a new segment of the yarn grouping is ready in the field 31 to be photographed. It has been shown to be advantageous for the field 31 to be of such a size that a complete winding volume without overlapping is recorded with each photograph with a five-time shift of the yarn grouping. This ensures a nearly uninterrupted, and in any case non-multiple recording of the yarn length which is present in the wind-up unit 3. After completion of a sequence of 5 photographs, the entire yarn length wound around the rollers 15 and 16 is measured by the measuring instrument. For this purpose, the entire photographed yarn length is reeled through until a new length of yarn is available to be photographed. This is necessary in order to avoid having the same yarn segments analyzed twice by the measuring device, thus producing misreadings in the measuring process.

Figure 4:
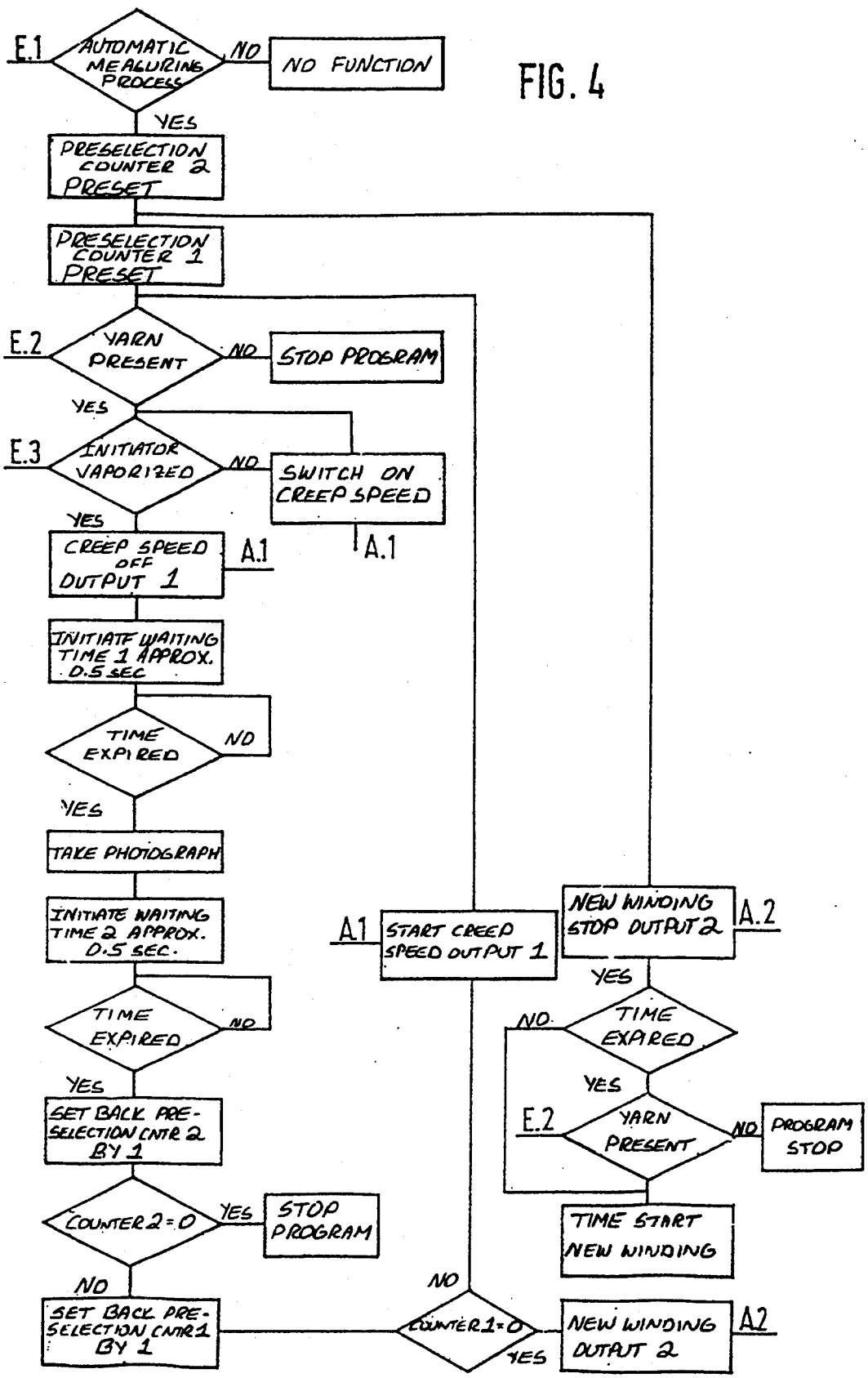
FIG. 4 shows a flow-chart for the control of the device for optical yarn analysis.

FIG. 4 shows a flow-chart for the control of the wind-up unit 3. The system receives a starting signal via input E1. A determination is made in preselection counter 2, as to the number of photographs after which the automatic measuring sequence is to be stopped. It can be adjusted at the user level in computer 8. In a preselection counter 1, the determination is made as to how many photographs are to be taken before a new wind-up operation is to take place. It has been shown to be advantageous for this counter to set at the number 5. This preselection counter means that 5 photographs are taken in order to cover the entire volume of windings. In the example shown, this counter can be changed only in the program, and not at the user level. This counter is of course also dependent on the size of the measuring field 31 to be measured, as well as on the size of a yarn winding. The length of the measuring field 31, multiplied by the preselection counter 1, should give substantially the length of the winding. This ensures that the wound-up yarn is examined essentially over its entire length.

If the controls find that no yarn is present at the input E2, the program is stopped. If the signal indicating the presence of yarn is received by the input E2, a verification is carried out to find out whether the initiator 29 is vaporized or not. This signal is transmitted to the controls via input E3. If the initiator 29 is not vaporized, i.e. if the yarn winding is not positioned at a predetermined location, a signal is transmitted to an output A1 to switch motor 27 to creep speed. The system then queries again whether the initiator 29 is vaporized. As soon as this is done a signal is transmitted to the output A1 indicating that the creep sped of the motor is to be switched off. After a waiting period of approximately 0.5 seconds which is provided for the yarn to settle down after coming into the desired position, a photograph is taken. After this photograph, a waiting period 2 of e.g. approx. 5 seconds is initiated. This waiting period 2 is used to process the picture. During that time the image recorded by the camera 5 is prepared for further processing and for analysis in an image processing system.

At the end of the waiting period 2, the preselection counter 2 which indicates the total number of photographs of the automatic measuring process is set back by one. As soon as the preselection counter 2 has reached value 0 the program is stopped. If the preselection counter 2 has not yet reached value 0, the preselection counter 1 which is set to the value 5, as described above for the shown embodiment, is set back by one. As long as the preselection counter 1 has not yet reached value 0 the creep speed of the motor 27 is switched on and the process starts again with the query of input E2.

If however the value of the preselection counter 1 is 0, a signal is transmitted via output A2 to the motor 27, prompting the latter to produce a new winding of the wind-up unit 3 by running at the main winding speed. The motor 27 runs for a predetermined period of time for the new winding. This period of time depends on the size of the wind-up unit 3 and must in any case be of sufficient duration for the wind-up unit 3 to be covered with new yarn 30. During the running of motor 27 at main winding speed, the input E2 is queried on the presence of a yarn. If no yarn is present, i.e. if a yarn breakage has occurred, the program is stopped. At the end of the winding period the motor 27 is stopped. The preselection counter 1 is again set to value 5 and the program starts anew.

Figure 5:
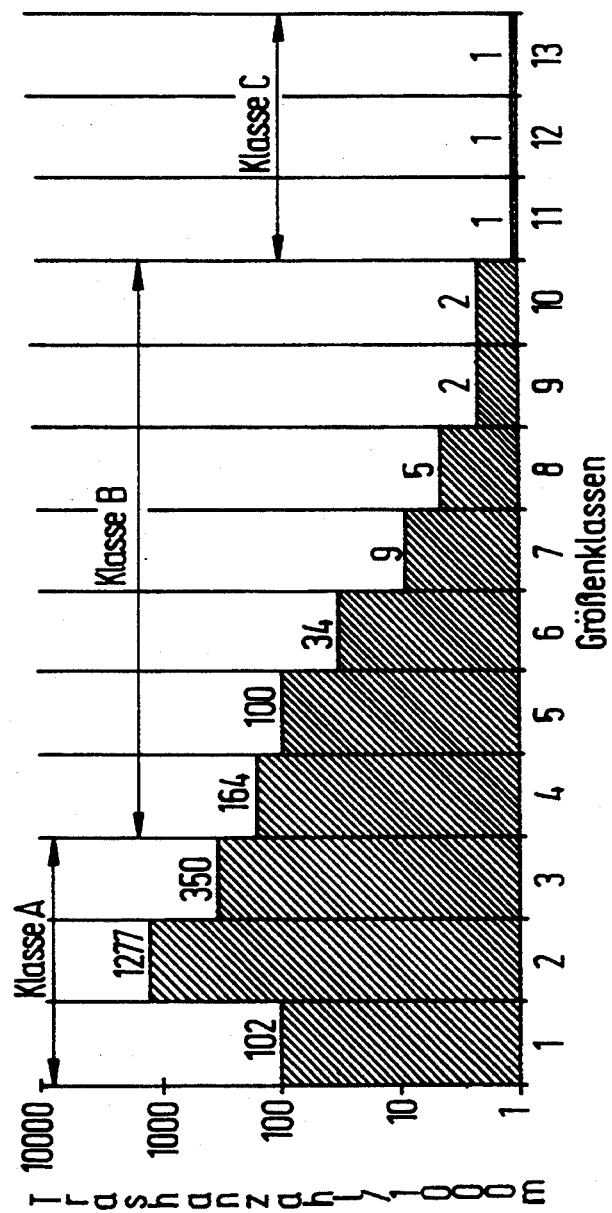
FIG. 5 shows the results of a trash analysis of the yarn.

FIG. 5 shows an evaluation of an analyzed yarn. In this analysis the yarn was examined for its trash contents. The found trash particles were divided into different size classes. The first 12 size classes contain trash particles measuring from 0 to 12 $mm^2$, with each size class covering a range of 0.1 $mm^2$. In this example, the sizes of trash particles in size class 13 range from 1.2 to 5 $mm^2$. The analysis shows that most trash particles were found in size class 2. In order to simplify the information on trash contents in the yarn, these 13 size class were subdivided into 3 characteristic classes. Class A in this case contains the small trash particles, class B the medium-size trash particles and class C the large trash particles.

In order to ascertain the size of trash particles found, a calibration of the system must be carried out at the beginning of the analysis process. This means that a predetermined size is provided with the appropriate scale and is entered into the system so that the latter may ascertain the size of the found trash particles and classify them accordingly into their size classes.

The detection of the trash particles is based on different gray graduations which the system recognizes. It has been shown to be advantageous to use an image processing device capable of distinguishing 256 grey graduations. In order to define which grey tones should be recognized by the image processing device as being trash particles, a certain threshold value of the grey graduations is set in the program.

By setting the given threshold value, the system is caused to blur the difference between the yarn grouping and the background surface so that only the dark trash particles can be recognized. The threshold value is adjusted so that all the trash particles if possible can be recognized on the graphic screen. The linked points, so-called pixels, which are recognized as trash particles are gathered together as surfaces in the computer, are sorted according to size and are classified into the different size classes and are stored.

The process and the device can be used in particular for quality control of a produced yarn or to detect adjustment errors in the spinning machine. It has furthermore been proven to be advantageous in determining the utilization of the correct raw material. Such a detection of yarn defects ensures advantageous further processing of the yarn.

It will be apparent to those skilled in the art that various modifications and variations can be made in the present invention without departing from the scope or spirit of the invention. Thus, it is intended that the present invention cover such modifications and variations as come within the scope of the appended claims and their equivalents.

We claim:

1. A process for detecting and counting yarn defects in a yarn segment, said process comprising the steps of:
    disposing a segment of predetermined length of yarn in front of a predetermined background surface, the background surface being of a color to enhance the visibility of yarn defects in the yarn;

illuminating the segment of yarn in front of the background surface with an illumination intensity which is dependent on the thickness or color of the yarn;

photographing the yarn segment in front of the background surface with a camera and digitizing the photographed image in a computer by way of an image processing program;

filtering out low contrast points from the digitized image which do not correspond to yarn defects;

categorizing and sorting by predetermined size classes the remaining contrast points corresponding to yarn defects; and generating a readout of the categorized yarn defects for subsequent analysis.

2. The process as in claim 1, further comprising cleaning the background surface before said photographing.

3. The process as in claim 1, further comprising illuminating the segment of yarn from above the background surface in the direction of the camera.

4. The process as in claim 1, further comprising illuminating the segment of yarn with a homogeneously radiating light source.

5. The process as in claim 1, further comprising illuminating the segment of yarn with an infrared lamp.

6. The process as in claim 1, further comprising disposing the segment of yarn in front of the background surface in the form of a processed yarn product.

7. The process as in claim 1, further comprising winding subsequent segments of yarn from a bobbin for analysis so that a statistical ascertainment of the sum of yarn defects in the yarn on the bobbin is generated.

8. The process as in claim 7, wherein each individual segment of yarn in wound up in parallel windings in front of the background surface, in that a section of the parallel windings are photographed and then conveyed beyond the background surface wherein a subsequent contiguous segment of yarn is then wound up in parallel windings and analyzed and so forth until a continuous predetermined length of yarn form the bobbin has been analyzed.

9. A device for detecting and counting yarn defects in yarn supplied from a bobbin, said device comprising:

an apparatus for photographing and analyzing a segment of predetermined length of yarn;

a first roller and a second roller placed at a distance from each other below said photographing apparatus, one of said rollers being a driven roller, said rollers configured to convey continuous segments of yarn below said apparatus; and a parallel winding device configured with said rollers which directs said continuous segments of yarn into parallel windings around said rollers, the rollers disposed so that said parallel windings of yarn therebetween can be photographed and analyzed by said photographing apparatus.

10. The device as in claim 9, further comprising a background surface disposed between said rollers at a height so as to be below the parallel windings of yarn, said background surface comprising a color which enhances detection of defects in the yarn.

11. The device as in claim 10, further comprising a cleaning device disposed to clean said background surface.

12. The device as in claim 11, wherein said cleaning device comprises at least one blowing nozzle directed upon said background surface.

13. The device as in claim 9, further comprising a yarn tensing device disposed between said bobbin and said first roller.

14. The device as in claim 9, further comprising a yarn monitor disposed between said bobbin and said first roller.

15. The device as in claim 9, further comprising a yarn draw off device disposed after said second roller, said yarn draw off device configured to draw the parallel windings of yarn from said rollers after they have been photographed.

16. The device as in claim 15, wherein said second roller comprises said driven roller, said yarn draw off device comprising a drive roller which is indirectly driven by said second roller.

17. The device as in claim 15, further comprising a yarn monitor disposed between said second roller and said yarn draw off device.

18. The device as in claim 16, further comprising an initiator disposed generally at said first roller to signal yarn position.

19. The device as in claim 9, wherein said parallel winding device comprises a separator disposed between said rollers.

20. The device as in claim 9, further comprising a background surface disposed between said rollers, and wherein said photographing apparatus comprises a camera disposed above said background surface.

21. The device as in claim 20, further comprising a light source disposed above said background surface.

22. The device as in claim 21, wherein said light source has a variable intensity.

23. The device as in claim 21, wherein said light source comprises a homogeneous light.

24. The device as in claim 21, wherein said light source comprises an infrared lamp.

25. The device as in claim 20, further comprising a light-tight housing, said rollers, background surface, and cameral disposed within said housing.

* * * * *